(12) United States Patent
Yuki et al.

(10) Patent No.: US 10,576,472 B2
(45) Date of Patent: Mar. 3, 2020

(54) CONTAINER FOR SPECIMEN DILUTION

(71) Applicant: SEKISUI MEDICAL CO., LTD., Chuo-ku (JP)

(72) Inventors: Kumiko Yuki, Adachi-ku (JP); Hiroaki Taira, Ushiku (JP)

(73) Assignee: SEKISUI MEDICAL CO., LTD., Chuo-ku (JP)

( * ) Notice: Subject to any disclaimer, the term of this patent is extended or adjusted under 35 U.S.C. 154(b) by 196 days.

(21) Appl. No.: 15/528,358

(22) PCT Filed: Nov. 20, 2015

(86) PCT No.: PCT/JP2015/082641
§ 371 (c)(1),
(2) Date: May 19, 2017

(87) PCT Pub. No.: WO2016/080509
PCT Pub. Date: May 26, 2016

(65) Prior Publication Data
US 2018/0043354 A1 Feb. 15, 2018

(30) Foreign Application Priority Data
Nov. 21, 2014 (JP) .................. 2014-236720

(51) Int. Cl.
*G01N 1/00* (2006.01)
*B01L 3/00* (2006.01)
*G01N 1/38* (2006.01)

(52) U.S. Cl.
CPC ............... *B01L 3/508* (2013.01); *G01N 1/38* (2013.01); *B01L 2300/046* (2013.01); *B01L 2300/0851* (2013.01); *B01L 2300/0858* (2013.01)

(58) Field of Classification Search
CPC ....................................................... G01N 1/00
See application file for complete search history.

(56) References Cited

U.S. PATENT DOCUMENTS 4,316,872 A 2/1982 Rahm et al.
4,720,374 A 1/1988 Ramachandran
(Continued)

FOREIGN PATENT DOCUMENTS

CN 1105305 C 4/2003
GB 2 472 384 A 2/2011
(Continued)

OTHER PUBLICATIONS

International Search Report dated Feb. 16, 2016 in PCT/JP2015/082641 filed Nov. 20, 2015.
(Continued)

*Primary Examiner* — Jyoti Nagpaul
(74) *Attorney, Agent, or Firm* — Oblon, McClelland, Maier & Neustadt, L.L.P.

(57) ABSTRACT

Provided is a container for preparing a diluted solution of a biological sample to be used for biological sample analysis. Specifically, provided is a container for specimen dilution, including: an open; a first bottom; a second bottom formed on an inner side wall of the container; and a groove upwardly formed, on the inner side wall of the container, from the second bottom, in which the groove has a constant width equal to a width of the second bottom, or the groove has, at a lower end thereof, a width equal to the width of the second bottom and upwardly widens.

20 Claims, 6 Drawing Sheets

(56) References Cited

U.S. PATENT DOCUMENTS

| | | | |
|---|---|---|---|
| 4,980,293 A | 12/1990 | Jeffs | |
| 5,310,527 A | 5/1994 | Romanauskas et al. | |
| 5,462,881 A | 10/1995 | Perlman | |
| 5,882,594 A | 3/1999 | Kawaguchi et al. | |
| 8,342,041 B2 * | 1/2013 | Massaro | B01L 3/502 |
| | | | 436/177 |
| 9,316,656 B2 * | 4/2016 | Sarofim | B01L 3/5025 |
| 2005/0136546 A1 | 6/2005 | Berndt et al. | |
| 2007/0217955 A1 | 9/2007 | Kawahara et al. | |

FOREIGN PATENT DOCUMENTS

| | | |
|---|---|---|
| JP | 55-161242 U | 11/1980 |
| JP | 4-348250 A | 12/1992 |
| JP | 6-277559 A | 10/1994 |
| JP | 10-62432 A | 3/1998 |
| JP | 2003-106958 A | 4/2003 |
| JP | 2003-161675 A | 6/2003 |
| JP | 2005-177749 A | 7/2005 |
| JP | 2007-279018 A | 10/2007 |
| JP | 2012-115829 A | 6/2012 |

OTHER PUBLICATIONS

Combined Office Action and Search Report dated Jan. 2, 2019 in Chinese Patent Application No. 201580063152.9, 14 pages (with unedited computer generated English translation and English translation of categories of cited documents).

Office Action dated Oct. 8, 2019 in corresponding Japanese Patent Application No. 2016-560296 (with machine translation), citing document AO therein, 9 pages.

Extended European Search Report dated Apr. 12, 2018 in European Patent Application No. 15860503.0 citing documents AA-AC and AO therein, 11 pages.

* cited by examiner

Fig.3(a)　　　　　　　Fig.3(b)
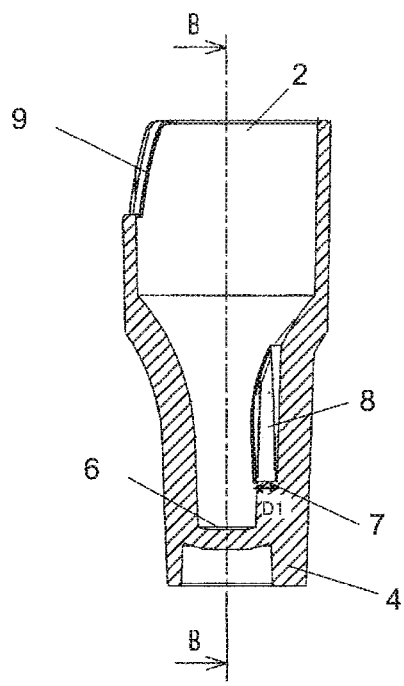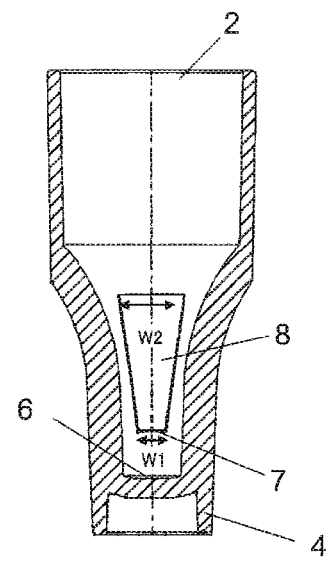
Fig.3(c)　　　　　　　Fig.3(d)
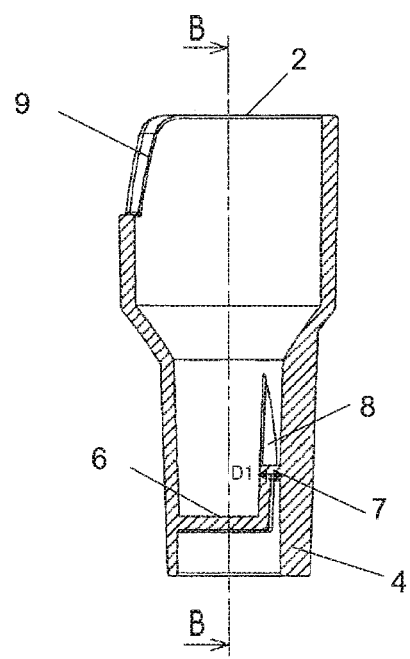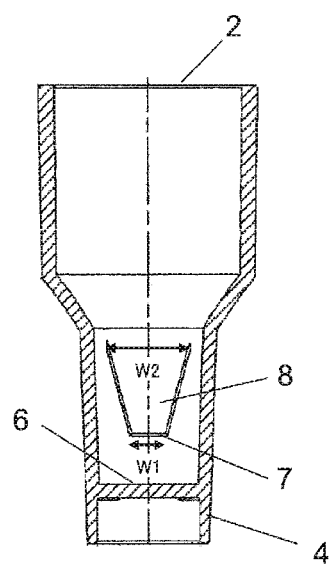

CONTAINER FOR SPECIMEN DILUTION

FIELD OF THE INVENTION

The present invention relates to a container for specimen dilution, which is used for biological sample analysis.

BACKGROUND OF THE INVENTION

Various types of automatic blood analyzing apparatus capable of analyzing a blood sample in a short period of time have been developed and put into practice. However, collected blood is not analyzed as it is, and is normally used for a variety of analyses after the blood is diluted. In addition, for analyses with high accuracy, it is necessary to sufficiently mix the blood and a diluting solution in order to precisely dilute the blood to a desired concentration. Therefore, it is desired that the automatic blood analyzing apparatus include means for mixing or stirring the blood and the diluting solution. For example, in Patent Literature 1, there is disclosed a liquid mixing container for diluting a blood sample. The liquid mixing container having a roughened inner wall contains a liquid injection port formed in an upper thereof, for feeding a diluting solution, and an air injection port formed in a bottom thereof, for injecting air for stirring a liquid. Further, in Patent Literature 2, there is disclosed a system for diluting and mixing a specimen such as blood by discharging the specimen and a diluting solution into a container, and then repeatedly sucking and discharging the liquid in the container using liquid distribution means. In Patent Literature 3, there is disclosed a cuvette for centrifugal stirring. The cuvette has a reagent accommodation formed in a bottom thereof, and a pocket having a sloped wall, formed in a part of a side wall thereof.

CITATION LIST

Patent Literature

[PTL 1] JP-A-2003-161675
[PTL 2] JP-A-10-62432
[PTL 3] JP-A-04-348250

SUMMARY OF THE INVENTION

Technical Problem

In the preparation of a diluted solution of a biological sample, for example, blood as described above, when positions onto which the biological sample was dropped varied, including a bottom of a container and an inner side wall of the container, the biological sample and a diluting solution were not sufficiently mixed at some of the positions onto which the biological sample had been dropped. It is an object of the present invention to provide means for preparing a diluted solution of a biological sample (specimen) to be used for biological sample analysis.

Solution to Problem

In order to achieve the above-mentioned object, the present invention provides a container for specimen dilution, which is capable of easily mixing a trace of a liquid biological sample and a diluting solution.

That is, according to a first aspect of the present invention, there is provided a container for specimen dilution, comprising:

an open upwardly opening;
a first bottom;
a second bottom formed on an inner side wall of the container; and
a groove upwardly formed, on the inner side wall of the container, from the second bottom,
wherein the groove has a constant width equal to a width of the second bottom, or the groove has, at a lower end thereof, a width equal to the width of the second bottom and upwardly widens.

The container for specimen dilution according to one embodiment of the present invention further comprises an open window formed in an upper end of a side wall opposed to the inner side wall on which the second bottom is formed.

In the container for specimen dilution according to one embodiment of the present invention, the second bottom has a width of from 1 mm to 3 mm and a depth of from 1 mm to 3 mm.

The container for specimen dilution according to one embodiment of the present invention further comprises a lid for closing the open. In another embodiment, the lid has a hole allowing passage of an injection tube for injecting a liquid into the container for sample dilution, or the lid has a film capable of being pierced through by the injection tube.

The container for specimen dilution according to one embodiment of the present invention further comprises an engaging member for retaining the container for specimen dilution on a rack.

According to another aspect of the present invention, there is provided a method of preparing a diluted solution of a biological sample, comprising: dropping a biological sample onto the second bottom of the container for specimen dilution; and injecting a diluting solution into the container after the dropping of the biological sample.

Advantageous Effects of Invention

According to the present invention, when the biological sample is dropped onto a specific position in the container, it is possible to easily prepare a homogeneous diluted solution of a trace of the biological sample. Therefore, the present invention enables analysis results to be obtained with high accuracy in biological sample analysis using the trace of the biological sample.

BRIEF DESCRIPTION OF DRAWINGS

FIG. 1 are views of a container for specimen dilution according to one embodiment of the present invention.

FIG. 3 (a) and FIG. 3 (b) are views of a container for specimen dilution according to one embodiment of the present invention, in which FIG. 3(a) is a sectional view taken along the line A-A of FIG. 2a and FIG. 3(b) is a sectional view taken along the line B-B of FIG. 3a. FIG. 3(c) and FIG. 3(d) are views of a container for specimen dilution according to another embodiment of the present invention, in which FIG. 3 (c) is a longitudinal sectional view and FIG. 3(d) is a sectional view taken along the line B-B of FIG. 3c. In each of FIG. 3(a) to FIG. 3(d), a dashed line indicates the vertical direction of the container.

DETAILED DESCRIPTION OF THE INVENTION

Figure 1A:
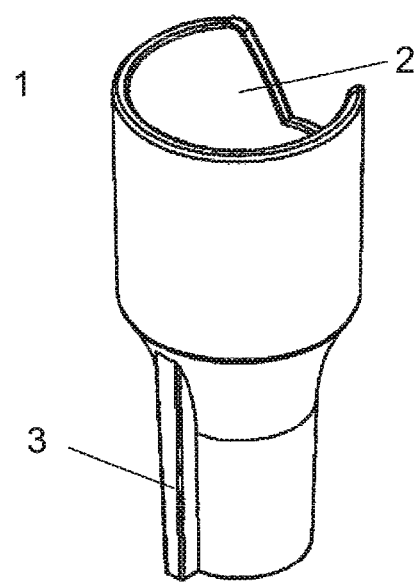
FIG. 1(a) is a top perspective view.

A container for specimen dilution according to the present invention is a container for preparing a specimen diluted solution to be used for biological sample analysis, for example, a blood test. More specifically, the container for specimen dilution according to the present invention is a container for preparing a diluted solution of a biological sample to be used as a sample serving as a measurement object in biological sample analysis. Examples of the biological sample (i.e., specimen) to be diluted in the container for specimen dilution according to the present invention include liquid biological samples, for example, body fluids, such as blood, serum, plasma, saliva, and urine, a solution or a suspension of feces or vomit, and a solution or a suspension of tissue and cells of animals and plants.

The container for specimen dilution according to the present invention is a container comprising an open and a bottom (first bottom), and further comprising a second bottom formed on an inner side wall of the container. The second bottom is a sample hold for holding a biological sample before dilution with a diluting solution. When the biological sample described above is dropped onto the second bottom, the biological sample is held there without flowing out of the second bottom. Then, when the diluting solution for the biological sample is injected into the container holding the biological sample in the direction of the side wall on which the second bottom is formed, the biological sample and the diluting solution are sufficiently mixed. Thus, a homogeneous diluted solution of the biological sample is prepared. When the biological sample is dropped onto the second bottom (sample hold), the mixing of the biological sample and the diluting solution can be promoted to provide a more homogeneous diluted solution of the biological sample as compared to the case where the biological sample is dropped onto a site other than the second bottom, for example, the case where the biological sample is dropped onto the first bottom.

The size of the container for specimen dilution according to the present invention may be changed as appropriate in accordance with the amount of the diluting solution to be injected. It is preferred that the container have a height of from about 30 mm to about 50 mm, a maximum inner diameter of from about 10 mm to about 20 mm, and such a volume that about 250 µL to about 500 µL of a liquid can be mixed or stirred to prepare a diluted solution. It is preferred that the container according to the present invention have a cylindrical shape, an inverse conical shape, a funnel shape, or a shape that is a combination thereof. It is also preferred that the container according to the present invention may be a freestanding container, and may have, for example, leg for freestanding.

The open of the container for specimen dilution according to the present invention upwardly opens. Herein, the upward side and downward side of the container refer to the upper side and lower side of the container standing with the first bottom at the bottom, respectively. The size of the open of the container according to the present invention is not particularly limited as long as the size allows the insertion of an injection tube (encompassing a needle, a nozzle, a capillary, a pipette tip, and the like) for dropping the biological sample onto the second bottom or for injecting a liquid such as the diluting solution. It is preferred that the open have an inner diameter of from about 10 mm to about 20 mm. The first bottom of the container for specimen dilution according to the present invention may be a flat bottom or a round bottom, or may have a shape that is a combination thereof.

The second bottom of the container for specimen dilution according to the present invention is a surface formed on the inner side wall of the container according to the present invention. The second bottom is preferably a substantially flat surface, and may be a curved surface. When the second bottom is a substantially flat surface, the flat surface is preferably a substantially non-sloped surface, and may be a substantially sloped surface. Herein, the non-sloped surface refers to a surface that is orthogonal to the vertical direction of the container according to the present invention (or a surface that becomes substantially horizontal when the container is allowed to stand vertically), and the sloped surface refers to a surface that is not orthogonal to the vertical direction of the container according to the present invention. Further, herein, the vertical direction of the container according to the present invention refers to the longitudinal direction of the container, which extends in the container from the first bottom to the open. In other words, the non-sloped surface is a surface that intersects the vertical direction of the container according to the present invention at an angle of 90°. It is preferred that the substantially sloped surface be a slope that intersects the vertical direction of the container according to the present invention at an angle of 60° or more and less than 90° and that is higher on an inner wall side of the container. When the second bottom is a curved surface, it is preferred that the curved surface be the above-mentioned substantially sloped surface, provided that the entirety of the surface forms a convex surface or a concave surface.

The shape of the surface forming the second bottom is not particularly limited, and examples thereof include a semi-circular arc shape, a U shape, a V shape, and a trapezoidal shape, which open to the inner side of the container. The size of the surface forming the second bottom only needs to be a size capable of holding 1 µL to 10 µL of the biological sample. It is preferred that the surface have a width (W1) of from 1 mm to 3 mm, for example, from 1 mm to 2 mm or from 2 mm to 3 mm, and a depth (D1) of from 1 mm to 3 mm, for example, from 1 mm to 2 mm or from 2 mm to 3 mm. It is more preferred that the surface have a width (W1) of from 1 mm to 2 mm and a depth (D1) of from 1 mm to 2 mm or from 2 mm to 3 mm, or that the surface have a width (W1) of from 2 mm to 3 mm and a depth (D1) of from 1 mm to 2 mm or from 2 mm to 3 mm. Herein, the width (W1) of the surface forming the second bottom is the length of a straight line connecting two points at which the surface and the inner wall surface of the container are brought into contact with each other, and the depth (D1) of the surface forming the second bottom is the maximum length of the surface in a direction orthogonal to the straight line.

The second bottom is formed above the first bottom and below the liquid level of the whole amount of the diluting solution to be injected so as to achieve a desired dilution factor. It is preferred that the second bottom be formed above the first bottom and below a discharge open of an injection tube for injecting the diluting solution or the like, and it is more preferred that the second bottom be formed about 3 mm to about 5 mm above the first bottom.

The container for specimen dilution according to the present invention further comprises a groove upwardly formed on the inner side wall from the second bottom. More specifically, the groove is a groove extending, with the second bottom as its base, on the inner side wall of the container according to the present invention along the vertical direction of the container, and opens to the inner side of the container and concave to the inner side surface thereof. Therefore, it is preferred that the shape of the groove may be a shape corresponding to that of the second bottom, for example, a semicircular shape, a U shape, a V shape, or a trapezoidal shape. During the dropping of the biological sample onto the second bottom, the groove facilitates visual recognition of the second bottom, and makes it easy to allow the distal end of the injection tube for dropping the biological sample to reach the second bottom.

The groove may have a constant width equal to the width of the second bottom, while the groove may have, at the lower end thereof, a width equal to the width of the second bottom and upwardly widen. For example, a width (W2) of the groove may be constant from the lower end to the upper end thereof and be equal to the width of the second bottom, preferably from 1 mm to 3 mm, for example, from 1 mm to 2 mm or from 2 mm to 3 mm. Further, for example, the width (W2) of the groove may be, at the lower end, equal to the width (W1) of the second bottom, preferably from 1 mm to 3 mm, more preferably from 1 mm to 2 mm, and gradually and upwardly widens, and be, at the upper end, preferably from more than 1 mm to 5 mm, more preferably from more than 2 mm to 5 mm. Further, for example, the width (W2) of the groove may be, at the lower end, equal to the width (W1) of the second bottom, preferably from 2 mm to 3 mm, and gradually and upwardly widens, and be, at the upper end, preferably from more than 2 mm to 6.5 mm, more preferably more than 3 mm to 6.5 mm.

Meanwhile, the groove is formed along the vertical direction of the container according to the present invention, and hence the length and depth of the groove may vary depending on the shape of the container according to the present invention and the thickness of the inner wall thereof. For example, when the shape of the container according to the present invention is an inverse conical shape or a funnel shape, the groove becomes gradually and upwardly shallower and may finally disappear. Meanwhile, when the shape of the container according to the present invention is a cylindrical shape, the depth of the groove may be constant. Further, when the shape of the container is a cylindrical shape, the groove may extend to the open, and may end at from 10 mm to 20 mm below the open or a lower position as long as the second bottom can be visually recognized from above the container, and the distal end of the injection tube for dropping the biological sample can reach the second bottom.

A container for specimen dilution according to a preferred embodiment of the present invention further comprises an open window formed in an upper end of a side wall opposed to the side wall on which the second bottom is formed. It is preferred that the window have no upper edge and form a continuous open communicating to the open of the container according to the present invention described above. By virtue of the window, when the biological sample is dropped from the injection tube, an operator can visually recognize the second bottom easily, and the dropping of the biological sample becomes easy. As the shape of the window, there are given a quadrilateral shape, a trapezoidal shape, a semicircular shape, and the like, and the shape of the window is not limited thereto as long as the second bottom can be visually recognized from above the container. The size of the window is also not particularly limited as long as the second bottom can be visually recognized, and the size may vary depending on the shape of the container according to the present invention. However, the maximum values for a width (W3) of the window and a height (H) thereof are each preferably from 7 mm to 15 mm, more preferably from 7 mm to 10 mm. Herein, the height (H) of the window is the maximum length thereof in the vertical direction of the container according to the present invention, and the width (W3) of the window is the maximum length thereof in the direction orthogonal to the height direction.

A container for specimen dilution according to a preferred embodiment of the present invention further comprises a lid for closing the open. As types of the lid, there are given a cap, a screw cap, a lid, and the like. It is preferred that the lid may have an open or a slit in a surface through which the injection tube passes, so as to allow the injection tube for injecting a liquid such as the diluting solution to be inserted into the container according to the present invention. The open or the slit is not particularly limited as long as the size and shape thereof allow the passage of the injection tube. Alternatively, the lid may have, in the surface through which the injection tube passes, a film capable of being pierced through by the injection tube.

A container for specimen dilution according to a preferred embodiment of the present invention further comprises an engaging member for retaining the container on a rack. The shape and size of the engaging member, and its arrangement on the container according to the present invention are not particularly limited as long as the engaging member allows the container according to the present invention to be stably fixed onto the rack. The engaging member is, for example, a protrusion or a hook arranged on the external surface of the container according to the present invention. It is preferred that the engaging member be an elongated protrusion arranged on an outer wall of the container according to the present invention along the longitudinal direction thereof. The container according to the present invention retained on the rack through the use of the engaging member is arranged in a predetermined direction with respect to the rack, and hence the container according to the present invention can be placed in a predetermined direction in an analyzing apparatus by setting the rack to a predetermined position in the apparatus.

In a preferred embodiment, as materials for the container for specimen dilution according to the present invention and the engaging member, there are given polypropylene, polyethylene, polystyrene, a polymethyl methacrylate resin, polyethylene terephthalate, polyamide, polybutylene terephthalate, polyacetal, and a combination thereof. It is preferred that the container according to the present invention and the engaging member be formed by injection molding. The lid and the engaging member may be formed integrally with the container according to the present invention, or may be separately formed and then connected thereto. It is preferred that the engaging member be formed integrally with the container according to the present invention.

In a preferred embodiment, as a material for the lid of the container for specimen dilution according to the present invention, there are given linear low-density polyethylene, polypropylene, high-density polyethylene, low-density polyethylene, polyamide, polyacetal, and a combination thereof. As a material for the surface of the lid through which the injection tube passes, there are preferably given linear low-density polyethylene, polypropylene, high-density polyethylene, low-density polyethylene, polyamide, polyacetal, and a combination thereof. As a material for the film of the lid, there are preferably given linear low-density polyethylene, polypropylene, high-density polyethylene, low-density polyethylene, polyamide, polyacetal, and a combination thereof. Further, it is preferred that the film be a thin layer capable of being easily pierced through by the injection tube. It is preferred that the lid and the film be formed by injection molding.

It is preferred that the biological sample be dropped into the container for specimen dilution according to the present invention manually. As an example, there is given a use method in which an operator, while holding the container for specimen dilution according to the present invention with one hand, adds the biological sample with a pipette or the like. In this case, the container according to the present invention may be held at an arbitrary angle that allows visual recognition of the second bottom through the open or the window.

The diluting solution may be injected into the container for specimen dilution according to the present invention manually or automatically. During the injection of the diluting solution, it is preferred that the discharge opening of the injection tube for injecting the diluting solution be directed to the second bottom. As an example of the case where the diluting solution is injected into the container according to the present invention automatically, there may be given discharge of the diluting solution onto the second bottom using a side-opening needle. Further, when the diluting solution is injected into the container according to the present invention automatically, it is preferred that a sign to be recognized by an apparatus for transferring the container or a diluting solution injecting apparatus be provided to a rack in which the container according to the present invention is accommodated.

The diluted solution of the biological sample (specimen) prepared using the container for specimen dilution according to the present invention can be set in and analyzed by a general analyzing apparatus as it is. It is more preferred that the container for specimen dilution according to the present invention be set in the analyzing apparatus under a state in which the biological sample is received in the container, and that a series of processes, which encompasses preparation and analysis of a diluted solution of the biological sample, be performed in the analyzing apparatus automatically or semi-automatically. The diluted solution of the biological sample prepared with the container for specimen dilution according to the present invention is applicable to a variety of biological sample analyses using a high performance liquid chromatograph, a biochemical automatic analyzing apparatus, a hematocytometer, flow cytometry, a flow injection apparatus, a grain size measuring apparatus, and the like.

Example

Now, aspects of the present invention are described in more detail with reference to the drawings. Embodiments of the present invention illustrated in the drawings are merely examples of the present invention, and the present invention is not limited to those embodiments. Needless to say, in addition to the matters directly described in the embodiments, the present invention encompasses various improvements and modifications that may be made by a person skilled in the art within the scope of claims.

Figure 1B:
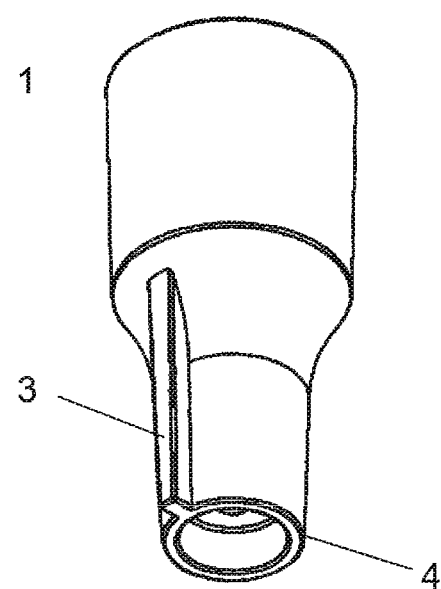
FIG. 1(b) is a bottom perspective view.

FIG. 1 are views of a container for specimen dilution according to one embodiment of the present invention. FIG. 1a and FIG. 1b are a top perspective view and a bottom perspective view, respectively, of a container 1 for specimen dilution according to the present invention. The container 1 for specimen dilution illustrated in FIG. 1 is a container comprising a lower portion of a funnel shape and an upper portion of a cylindrical shape, and comprises an open 2 upwardly opening. Through the open 2, an injection tube for injecting a biological sample or a diluting solution is inserted into the container 1. On an outer wall of the container 1, an engaging member 3 is arranged along the longitudinal direction of the container according to the present invention. The container 1 is capable of freestanding by virtue of leg 4.

Figure 2A:
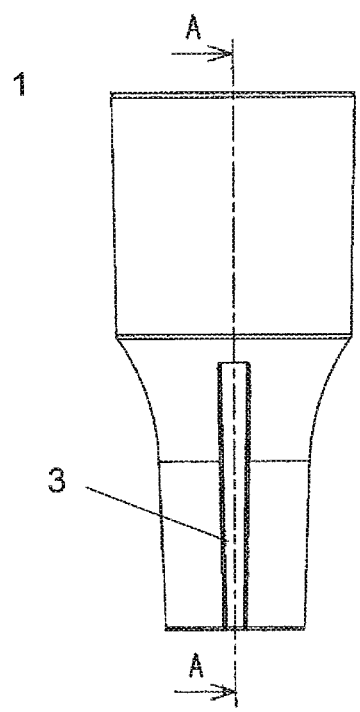
FIG. 2(a) is a front view of the container for specimen dilution according to the present invention illustrated in FIG. 1.
Figure 2B:
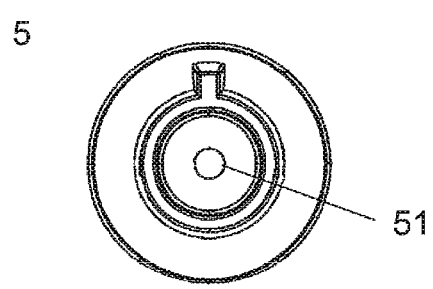
FIG. 2(b) is a top view of a lid.

FIG. 2a is a front view of the container 1 for specimen dilution according to the present invention, and FIG. 2b is a view of a lid 5 of the container 1 according to one embodiment of the present invention. The lid 5 has an opening 51 allowing the passage of the injection tube for injecting the diluting solution for the biological sample. FIG. 3a and FIG. 3b are a sectional view of the container 1 taken along the line A-A of FIG. 2a, and a sectional view of the container 1 taken along the line B-B of FIG. 3a, respectively. As illustrated in FIG. 3a, the container 1 comprises a first bottom 6, which is an approximately flat bottom. Further, in FIG. 3a, a side sectional view of a second bottom 7 formed on an inner side wall of the container 1 and a groove 8 upwardly extending therefrom is illustrated. Meanwhile, in FIG. 3b, a front view of the second bottom 7 and the groove 8 is illustrated. The second bottom 7 illustrated in FIG. 3a and FIG. 3b is a horizontal flat surface, and the groove 8 is a groove that upwardly widens with the second bottom 7 at its base. The groove 8 is deepest at the lower end thereof, and becomes gradually and upwardly shallower to finally disappear.

FIG. 3c and FIG. 3d are sectional views of a container 1 for specimen dilution according to another embodiment of the present invention. FIG. 3c is a longitudinal sectional view of the container 1, and FIG. 3d is a sectional view of the container 1 taken along the line B-B of FIG. 3c. As illustrated in FIG. 3c, the container 1 comprises the first bottom 6, which is an approximately flat bottom. The second bottom 7 formed on the inner side wall of the container 1 is a horizontal flat surface, and the groove 8 is a groove that upwardly widens with the second bottom 7 at its base.

Figure 4:
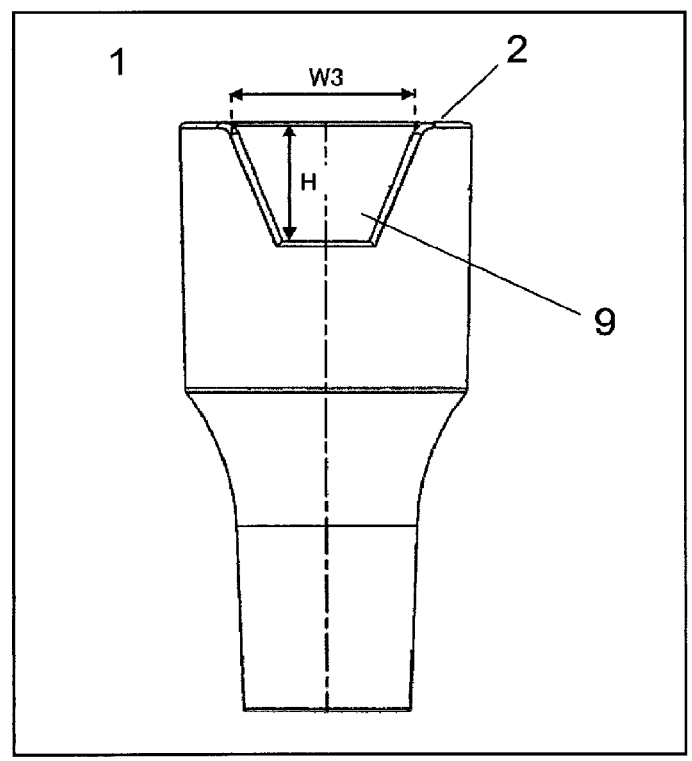
FIG. 4 is a back view of the container for specimen dilution according to the present invention illustrated in FIG. 1. A dashed line indicates the vertical direction of the container.

FIG. 4 is a back view of the container 1 for specimen dilution according to the present invention. In FIG. 4, a window 9 arranged in the upper end of a side wall of the container 1 is illustrated. As illustrated in FIG. 2a, the window 9 is arranged in a side wall opposed to the side wall on which the second bottom 7 is formed. The window 9 illustrated in FIG. 4 is a window with no upper edge, which is continuous with the open 2 at the upper end of the container 1.

Figure 5:
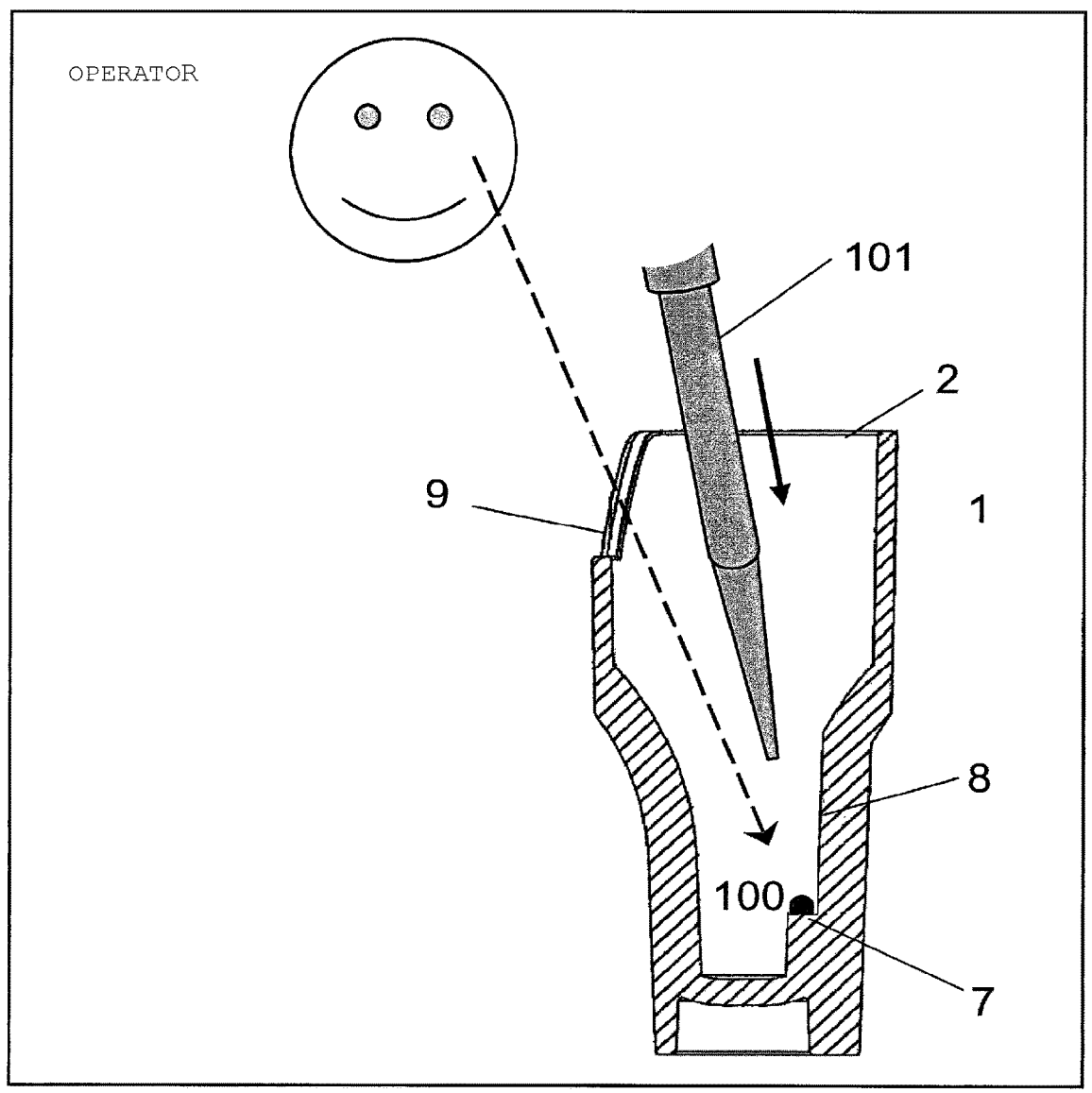
FIG. 5 is a conceptual view of an operation of dropping a blood sample into the container for specimen dilution according to the present invention.

FIG. 5 is a conceptual view of an operation of dropping a blood sample onto the second bottom 7 of the container 1 for specimen dilution according to the present invention. An operator drops a blood sample 100 onto the second bottom 7 by pipetting. A pipette tip 101 is inserted through the open 2, and the distal end thereof reaches the second bottom 7. During this operation, the presence of the window 9 and the groove 8 allows the operator to easily recognize the position of the second bottom 7 from above the container 1. Further, the presence of the groove 8 allows the distal end of the pipette tip 101 to easily reach the second bottom 7.

Figure 6:
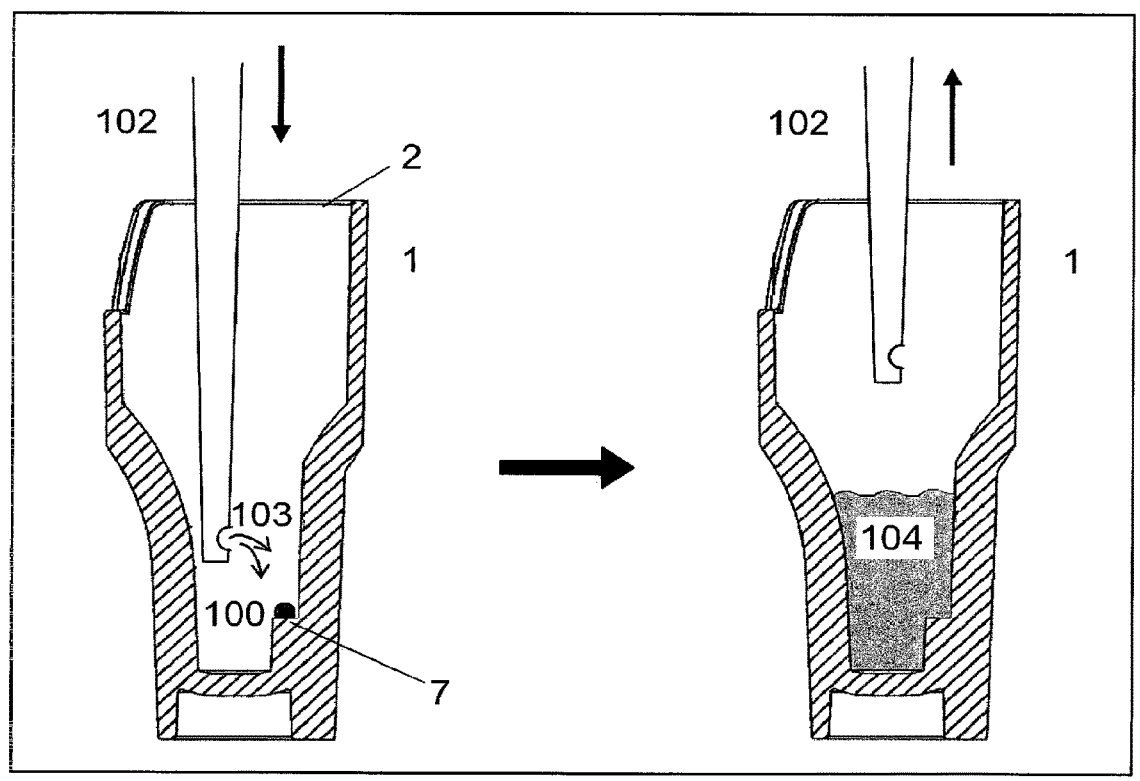
FIG. 6 is a conceptual view of an operation of diluting the blood sample in the container for specimen dilution according to the present invention.

FIG. 6 is a conceptual view of an operation of diluting the blood sample in the container 1 for specimen dilution according to the present invention. First, the blood sample 100 has been dropped onto the second bottom 7 in the container 1. Next, an injection tube 102 for injecting a diluting solution 103 is inserted into the container 1 through the open 2. The injected diluting solution 103 washes the blood sample 100 off the second bottom 7. The blood sample 100 that has flowed into the diluting solution is sufficiently mixed with the diluting solution, and thus a homogeneous diluted solution 104 of the blood sample is prepared.

Test 1

With the use of the container 1 for specimen dilution according to the present invention, a diluted solution was prepared from 3 µL of a blood sample by a hand method or an automatic analyzing apparatus. In Table 1, peak area values for hemoglobin A0, obtained by analyzing the prepared blood diluted solution by an HPLC method, are shown. In the dilution by the hand method, a pipette tip was used to discharge 300 µL of a diluting solution in the direction of the blood sample on the second bottom 7, and further, a mixture of the discharged diluting solution and blood was sufficiently stirred by being sucked and discharged 5 times. The automatic analyzing apparatus includes a side-opening needle as an injection tube for the diluting solution, and the direction of the container 1 for specimen dilution is fixed by the engaging member 3 arranged in the container 1 for specimen dilution. Thus, the diluting solution is discharged from the side-opening needle in the direction of the second bottom 7. In the dilution by the automatic analyzing apparatus, blood was dropped onto the first bottom 6 of the container 1, the second bottom 7 thereof, or the side wall thereof opposed to the second bottom 7, then the diluting solution was discharged from the side-opening needle in the direction of the second bottom 7, and further, a mixture of the discharged diluting solution and blood was sufficiently stirred by being sucked and discharged 5 times.

TABLE 1

|  | Hand method | Automatic analyzing apparatus | | |
| --- | --- | --- | --- | --- |
|  |  | First bottom | Second bottom | Side wall opposed to second bottom |
| Sample No. 1 | 21.85 | 9.37 | 22.55 | 16.64 |
| Sample No. 2 | 21.82 | 10.41 | 23.17 | 14.74 |
| Sample No. 3 | 22.61 | 12.57 | 20.13 | 19.58 |
| Average | 22.09 | 10.78 | 21.95 | 16.99 |

When the automatic analyzing apparatus including the side-opening needle as the injection tube for the diluting solution was used, only the group in which the blood sample was dropped onto the second bottom 7 exhibited a peak area comparable to that in the dilution by the hand method, demonstrating that a diluted solution having an appropriate concentration, in which blood and the diluting solution were sufficiently mixed, was prepared. Meanwhile, the group in which blood was dropped onto the first bottom 6 or the side wall opposed to the second bottom 7 exhibited a peak area lower than that in the dilution by the hand method, suggesting that blood and the diluting solution were not sufficiently mixed and thus the concentration of the diluted solution was lowered. Those results demonstrated that a homogeneous blood diluted solution was obtained when blood was dropped onto the second bottom 7 in the automatic analyzing apparatus including the side-opening needle.

REFERENCE SIGNS LIST

1 container for specimen dilution
2 open
3 engaging member
4 leg
5 lid
51 opening
6 first bottom
7 second bottom (sample hold)
8 groove
9 window
100 blood sample
101 pipette tip
102 injection tube
103 diluting solution
104 diluted solution

The invention claimed is:

1. A container for specimen dilution, comprising:
a container having an open at an upper end, a first bottom at a lower end, and an inner side wall extending between the open and the first bottom and having a groove,
wherein the inner side wall is formed such that the groove forms a second bottom in the inner side wall and has a depth having a deepest portion at the second bottom and becoming gradually shallower toward the upper end, and a constant width equal to a width of the second bottom, or a width widening from the second bottom toward the upper end.

2. The container for specimen dilution according to claim 1, wherein the container has an open window formed in the inner side wall at the upper end such that the open window is positioned on an opposite side with respect to the second bottom formed in the inner side wall.

3. The container for specimen dilution according to claim 2, wherein the second bottom has a width of from 1 mm to 3 mm and a depth of from 1 mm to 3 mm.

4. The container for specimen dilution according to claim 2, further comprising:
a lid configured to close the open.

5. The container for specimen dilution according to claim 4, wherein the lid has a hole configured to allow passage of an injection tube such that a liquid is injected into the container.

6. The container for specimen dilution according to claim 5, wherein the lid has a film that the injection tube pierces through.

7. The container for specimen dilution according to claim 2, further comprising:
an engaging member that retains the container on a rack.

8. The container for specimen dilution according to claim 1, wherein the second bottom has a width of from 1 mm to 3 mm and a depth of from 1 mm to 3 mm.

9. The container for specimen dilution according to claim 8, further comprising:
a lid configured to close the open.

10. The container for specimen dilution according to claim 9, wherein the lid has a hole configured to allow passage of an injection tube such that a liquid is injected into the container.

11. The container for specimen dilution according to claim 10, wherein the lid has a film that the injection tube pierces through.

12. The container for specimen dilution according to claim 8, further comprising:
an engaging member that retains the container on a rack.

13. The container for specimen dilution according to claim 1, further comprising:
   a lid configured to close the open.

14. The container for specimen dilution according to claim 13, wherein the lid has a hole configured to allow passage of an injection tube such that a liquid is injected into the container.

15. The container for specimen dilution according to claim 14, further comprising:
   an engaging member that retains the container on a rack.

16. The container for specimen dilution according to claim 14, wherein the lid has a film that the injection tube pierces through.

17. The container for specimen dilution according to claim 16, further comprising:
   an engaging member that retains the container on a rack.

18. The container for specimen dilution according to claim 13, further comprising:
   an engaging member that retains the container on a rack.

19. The container for specimen dilution according to claim 1, further comprising:
   an engaging member that retains the container on a rack.

20. The container for specimen dilution according to claim 1, wherein the groove is formed in the inner side wall such that the second bottom has a horizontal flat surface.

* * * * *